United States Patent [19]
Schon

[11] Patent Number: 6,066,760
[45] Date of Patent: May 23, 2000

[54] PROCESS FOR THE PREPARATION OF ALKANE SULFONIC ACID AND ALKANE SULFONYL CHLORIDE

[75] Inventor: Steven Gabriel Schon, Tredyffrin Township, Pa.

[73] Assignee: Elf Atochem North America, Inc., Philadelphia, Pa.

[21] Appl. No.: 08/221,224

[22] Filed: Mar. 31, 1994

[51] Int. Cl.[7] .................................................. C07C 309/04
[52] U.S. Cl. ........................................... 562/118; 562/829
[58] Field of Search ...................................... 562/118, 829

[56] References Cited

U.S. PATENT DOCUMENTS

| | | | |
|---|---|---|---|
| 3,600,136 | 8/1971 | Giolito et al. | 422/188 |
| 3,626,004 | 12/1971 | Guestin | 562/829 |
| 3,993,692 | 11/1976 | Giolito et al. | 260/543 |

FOREIGN PATENT DOCUMENTS 1350328  4/1974  United Kingdom .

OTHER PUBLICATIONS

Koch Engineering Co., Inc, "Static Mixing Technology" Bulletin KSM © 1991 p. 1–12.
Marske, et al., Water Sewage Workss (1973), 120 (1) 70–7.
F. Grosz—Roll et al., "Gas/Liquid Mass Transfer with Static Mixing Units", Fourth European Conf. on Mixing, Paper $F_2$ Apr. 27–29, 1982, pp. 225–236.
Perry's Chem. Engineer's Handbook, 6th Ed., "Reactor Designs": Basic Principals and Data, pp. 4–24 thru 4–27, McGraw–Hill Co.
Koch Engineering Company, Inc. "Static Mixing Technology" Bulletin KSM–6, © 1991, pp. 1–12.

*Primary Examiner*—Robert Gerstl
*Attorney, Agent, or Firm*—Gilbert W. Rudman; Stanley A. Marcus

[57] ABSTRACT

A process is disclosed for the efficient production of high purity alkane sulfonic acid and/or alkane sulfonyl chloride product wherein a compound of the formula RSX, where X is hydrogen or —$SR^1$ and R and $R^1$ are alkyl radicals is continuously reacted with chlorine in aqueous hydrochloric acid to produce a turbulent evolution of hydrochloride gas, passing the reactants through stationary mixing elements to promote plug-flow, and separately withdrawing a product. Apparatus for this process is also disclosed.

6 Claims, 2 Drawing Sheets

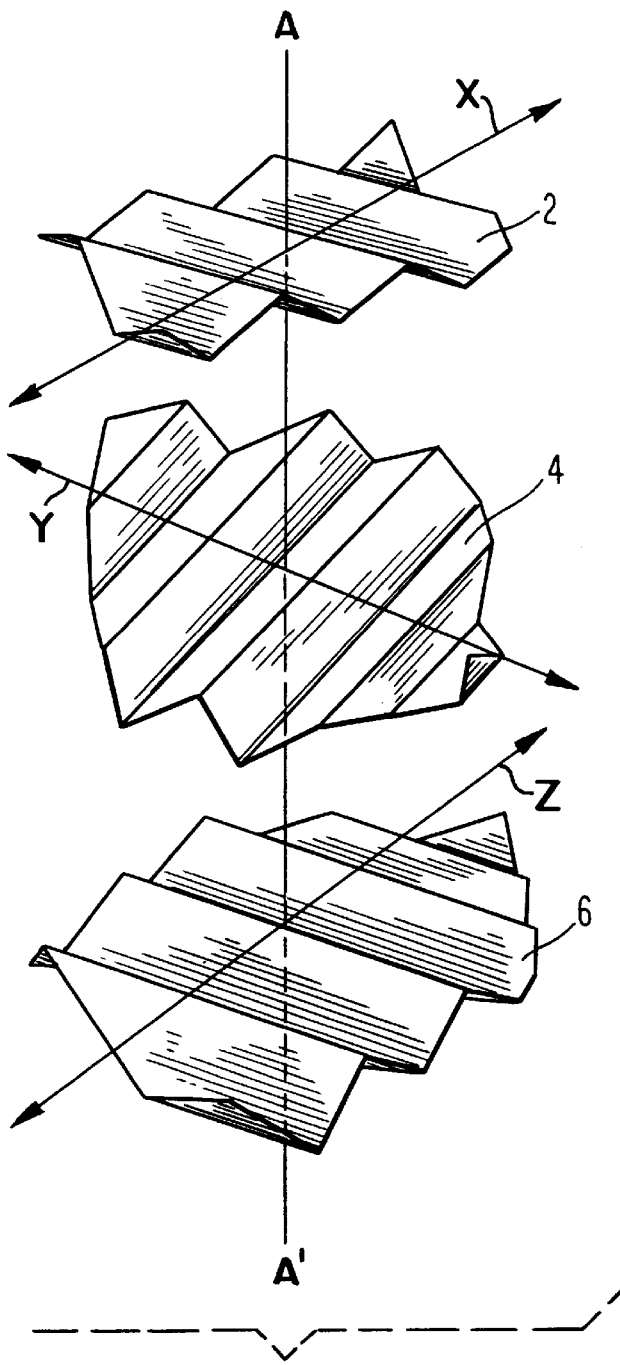
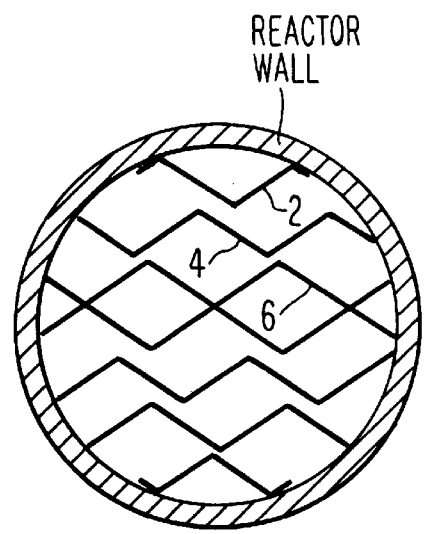
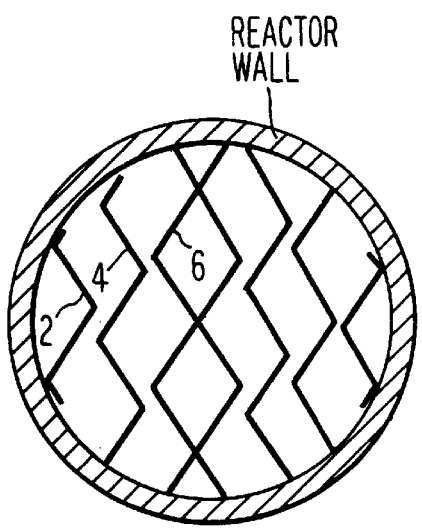
*Fig. 2*
*Fig. 3a*
*Fig. 3b*

6,066,760

PROCESS FOR THE PREPARATION OF ALKANE SULFONIC ACID AND ALKANE SULFONYL CHLORIDE

BACKGROUND OF THE INVENTION

This invention relates to a process for the continuous, preparation of high-purity alkane sulfonic acid and/or alkane sulfonyl chloride in a reaction zone containing stationary (motionless and rigid) mixing elements which promote plug-flow. More particularly, it relates to a continuous process for the preparation of alkane sulfonic acid and/or alkane sulfonyl chloride product from a sulfur compound of the formula RSX where X is hydrogen or—$SR^1$, and R and $R^1$ are alkyl groups having from 1 to 20 carbon atoms, reacted with chlorine in an aqueous medium wherein the fluids of the reaction flow through a vertical reaction zone free of mechanical moving agitating means and containing stationary mixing elements which promote plug-flow, and continuously, separately withdrawing hydrochloride gas and product.

THE PRIOR ART

Several prior disclosures teach the continuous preparation of alkane sulfonic acid and/or alkane sulfonyl chloride by reacting an alkyl mercaptan or alkyl disulfide with chlorine in an aqueous medium. For example, U.S. Pat. No. 3,600,136 issued Aug. 17, 1971; U.S. Pat. No. 3,626,004 issued Dec. 7, 1971; U.S. Pat. No. 3,993,692 issued Nov. 23, 1976; and U.K. Specification 1,350,328 published Apr. 18, 1974 disclose similar reactions. Each of these teachings include carrying out the reaction in a reactor designed to provide a high degree of "back-mixing". "Back-mixing" is a term used in the art and defined herein as the mixing of reactants of a chemical reaction flowing in an axial direction relative to the axis of the reaction zone whereby less than all of the reactants pass through the reaction zone of a continuous system over a given period of time. In this type of mixing, the reactants tend to continuously swirl back as the mass proceeds in the general direction of outflow, and the material at the center of the reactor travels at a faster rate than the material adjacent the reactor walls (wall drag). It is the nature of back-mixing that the effluent will always contain some fraction of unreacted feed (the residual decreases logarithmically with residence time). Back-mixing generally occurs with various methods employing dynamic mixing means, e.g., mechanical stirring and gas-induced turbulence.

"Back-mixing" may be contrasted to "plug-flow" which is defined herein as the mixing of reactants flowing in a radial direction relative to the axis of the reaction zone whereby all of the reactants pass through the reaction zone of a continuous system over a given period of time. In this type of mixing, the reactants swirl radially toward and away from the outer walls and the reactor axis as they move in the general axial direction of outflow. This radial motion promotes intimate contact of the reactants, even heating, and movement of the reactants at the same rate whereby all pass through the reaction zone in a specified elapsed time. Plug-flow generally occurs with tubular reactors, with or without packed catalyst beds or static mixers, but in the absence of dynamic mixing means and without the turbulent activity of the reactants which may promote back-mixing. "Plug-flow" and "back-mixing" are phenomena disclosed in the chemical engineering literature, e.g., "Perry's Chemical Engineer's Handbook" 6th Ed. pp. 4–24 through 4–52, and Bulletin KSM-6, Copyright 1991, Koch Engineering Company, Inc. The latter publication discusses plug-flow reactors and the role of stationary (motionless) mixing elements in reactors for use, for example, with low viscosity, turbulent flow-systems.

STATEMENT OF THE INVENTION

This invention is a process for the preparation of alkane sulfonic acid and/or alkane sulfonyl chloride product comprising continuously reacting a compound of the formula RSX, where X is hydrogen or a radical of the formula—$SR^1$ and R and $R^1$ are alkyl groups having one to 20 carbon atoms, with at least a stoichiometric amount of chlorine in a vertical reaction zone free of moving, mechanical agitating means and containing aqueous hydrochloric acid at a reactant feedrate at least sufficient to achieve a vigorous evolution of hydrochloride gas, passing the contents of said reaction zone through, and in contact with stationary mixing elements to promote plug-flow, withdrawing hydrochloride gas, and, separately withdrawing said product from the reactor.

THE DRAWING

FIG. 1 in the Drawing is a diagrammatic view depicting a specific apparatus embodiment for operation of the process of this invention, FIG. 2 is a partial, exploded, perspective view of one embodiment of a stationary (motionless) mixing element for packing into a section of a reaction zone of a reactor for this invention, and FIGS. 3a and 3b are cross-sectional, diagrammatic, 90° rotated views of an embodiment of the stationary mixing element or unit packed within a cylindrical reaction zone of a reactor column for this invention.

DETAILED DESCRIPTION OF THE INVENTION

Figure 1:
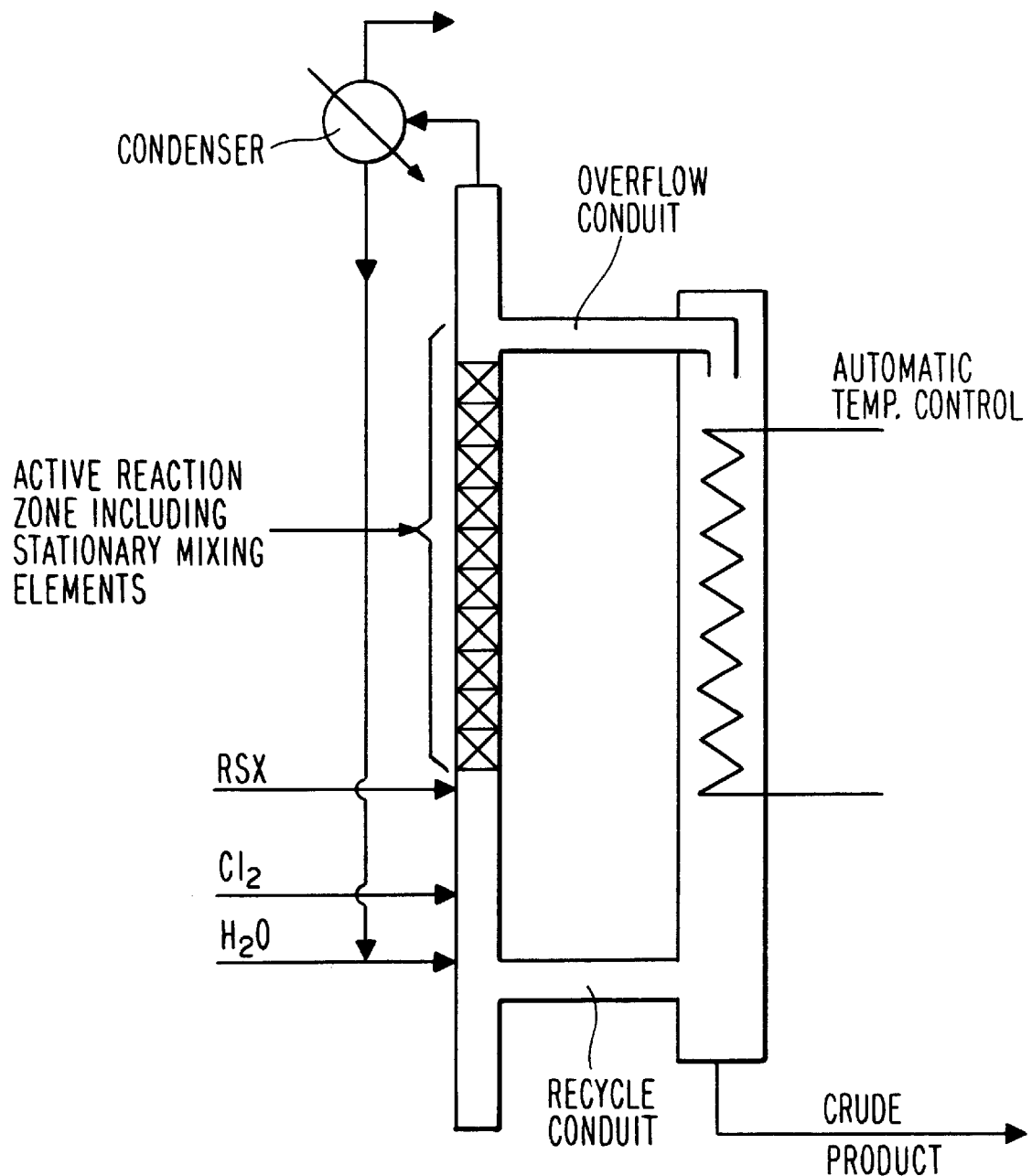

The process of this invention relates to the continuous preparation of alkane sulfonic acid, alkane sulfonyl chloride or mixtures thereof. These products are formed by the reaction of a compound having the formula RSX with chlorine gas in an aqueous medium and in the absence of mechanical agitation (moving, mechanical mixing means). The compound RSX is one in which X is hydrogen or—$SR^1$ and R and $R^1$ are the same or different alkyl groups having from one to twenty (20) carbon atoms, preferably one to 6 carbon atoms and most preferably methyl. Other alkyl groups include, for example, arachidyl, stearyl, lauryl, capryl, butyl, propyl, ethyl, and the like. The formula RSX represents alkyl mercaptan and alkyl (dialkyl) disulfides, respectively.

The reaction disclosed herein is continuous and conducted so that the reactant feed rate in the process causes vigorous evolution of hydrogen chloride gas and consequential mixing of the reactants. This phase of the process is generally disclosed, for example, in the aforementioned U.S. Pat. No. 3,626,004 and U.K. 1,350,328. However, these earlier disclosed processes are conducted with considerable back-mixing caused by recirculation of eddies and coalescence of gas bubbles within the reaction zone. In accordance with this invention the process is conducted so that the reactants are, while exposed to turbulent mixing from the vigorous evolution of gaseous hydrochloride, subjected to plug-flow by passing the reactants, as they move through the active reaction zone, through a static mixing system comprising multiple, stationary, rigid, fluid-mixing elements (or element) which enhance gas-liquid contact and radial mixing while minimizing back-mixing.

The temperature at which the reactions of this invention are conducted to form alkane sulfonic acid (ASA), alkane sulfonyl chloride (ASC) or mixtures of these, are well known in the art and, for the purposes of this invention, not critical. Generally, preparation of product which is predominantly ASC is carried out at a temperature within the range of about −10 to about +50° C. while ASA, in major amounts, is prepared at a temperature ranging from about 85° to 115° C. Substantially mixed products (ASA & ASC) are formed at temperatures within the range of over 50° to less than about 85° C.

The reactant feedrate, as governed by the continuous feed of the RSX compound to the reaction zone, is at least sufficient to achieve a vigorous evolution of hydrochloride gas. Preferably, the range of the feedrate is from about 0.005 pound-mole (lbmole) per hour (hr) per square foot ($ft^2$) of cross-sectional area of the active reaction zone up to about 12.0 lbmole /hr-$ft^2$. More preferably, from about 0.5 to about 8.0 lbmole/hr-$ft^2$ of RSX reactant is fed to the active reaction zone.

The process of this invention unexpectedly provides ASA and ASC product of substantially reduced oxidizable impurities. Oxidizable impurities are intermediates or unreacted components which are produced during manufacture or occur in the crude ASA or ASC. Examples of these oxidizable impurities are dialkyl disulfides and alkyl alkane thiosulfonates which, in amounts in excess of 5–20 parts per million (ppm), are undesirable product constituents since they can decompose into odoriferous compounds in end uses for the product, such as electrochemical applications. The prior art processes for manufacture of ASA and/or ASC produce undesirably large amounts of oxidizable impurities requiring further treatment of the crude ASA or ASC to reduce the oxidizable impurities to acceptable levels.

The procedures for preparing ASA and ASC of the prior art also suffer from inefficient gas-liquid contacting resulting in bypassing of reactant gases (mercaptan and chlorine) from the reaction medium thereby reducing the efficiency of raw material utilization. The process of this invention has the surprising benefit of improving gas-liquid contact and solubilization of the reactant gases thus substantially improving raw material utilization.

Furthermore, the invention produces the surprising effect of improving the reaction zone (reactor) volumetric efficiency, and reducing the minimum length of the active (turbulent) zone required for effective contact of the reactants. U.S. Pat. No. 3,626,004 teaches that a key operating parameter of its process is the RSX compound feedrate per unit volume. Utilization of the motionless mixing elements of this invention, unexpectedly, permits the feedrate to be essentially independent of the length (beyond the minimum length required for the stationary mixing elements) of the active reaction zone. Accordingly, the feedrate of the process of this invention is measured by the cross-sectional area, i.e. lbmole/hr- $ft^2$.

Still further, this invention substantially improves the hydrodynamic behavior of the reaction fluids, preventing coalescence of the turbulent gas bubbles, and eliminating back-mixing and recirculating eddies within the active reaction zone. These improvements serve to increase the practical upper limit on the reactor throughput before hydrodynamic effects (e.g., slugging, entrainment, vibration) limit reactor capacity.

An apparatus for carrying out the process of this invention is more specifically disclosed in FIG. 1 of the drawing which is similar (except for the stationary mixing elements) to the flow diagram of a reactor disclosed in the drawing of U.S. Pat. No. 3,626,004. FIG. 1 is suitable to represent reactors used to prepare ASC, ASA and mixtures of ASA and ASC. The critical process modification of this invention (passing the contents of the reaction zone through stationary mixing elements to provide plug-flow) is represented and labeled in the figure of the drawing as "Stationary Mixing Elements" situated within the "Active Reaction Zone".

In FIG. 1, chlorine gas ($Cl_2$) is continuously injected near the bottom of the reactor in an amount based on the feedrate of the RSX compound shown entering above the chlorine feed. The order of addition of RSX and $Cl_2$ is not critical; $Cl_2$ may be introduced above the RSX feed. The RSX compound is fed in an amount sufficient to achieve vigorous evolution of hydrochloride gas as the sulfur compound reacts with chlorine in the active reaction zone. Water or aqueous hydrochloric acid is fed in at the lower side of the reactor adjacent the recycle conduit. The active reaction zone is located above the feed ports for the RSX compound and chlorine and just below the overflow conduit of the system. The zone may extend in the reactor for a length ranging from about 0.5 to about 30 feet, preferably from about 1 to about 10 feet.

Parallel to the reactor is an overflow reservoir having fluid conduit means near the bottom and the top to receive and emit fluid from and to the reactor. Interposed within the reservoir is a heat exchange system to cool the overflow fluid. A product discharge line is shown at the bottom of the reservoir but may be positioned at any point in the reservoir side. At the top of the reactor a flow line is shown for vapors. These vapors may be discharged to scrubber columns (not shown) or may first pass through the condenser, as shown, and condensibles returned to the bottom of the reactor; the non-condensibles are then discharged from the top to a scrubber or other treatment.

The present invention provides an improvement in the purity of alkane sulfonic acid and/or alkane sulfonic chloride products utilizing a known gas-lift reactor, in past methods operated with considerable back-mixing, but improved by utilization of stationary mixing means to promote plug-flow.

While the stationary mixing elements situated within the active reaction zone of FIG. 1 are shown in multiple units or elements, a single unit may be fabricated to accomplish a similar result.

The preferred plug-flow inducing means of this invention may be described as stationary (rigid-motionless) mixing elements which fully occupy (pack) the reaction zone and cause the reaction mass to flow in radially intersecting paths while moving generally upward in the vertical reactor. Such elements for promoting static mixing are commercially available and include multi-layered devices comprising, for example, intersecting corrugated-plate, intersecting bar, helical ribbon, interacting elipse and combinations of these rigid configurations. The elements are usually manufactured in relatively short lengths compared to their widths, e.g., 1 unit of width (diameter) to 1 unit of length or, with large diameter reactors, greater in width than length. They may be fabricated with any rigid material including e.g., metal or heat-stable plastic. The elements may be prepared or coated with materials which act as chemical reaction catalysts. Advantageously, the elements are manufactured to a precise fit of the reactor and pack the reaction zone of the reactor. Multiple elements are packed head-to-head (concentrically) to substantially fill the reaction zone.

A preferred embodiment of the stationary mixing elements is depicted in FIGS. 2, 3a and 3b of the drawing. In FIG. 2, a stationary mixing element, preferably used for this invention, is partially shown in an exploded, perspective view wherein several corrugated sheets 2, 4 and 6 lie in parallel planes (represented by arrow-lines X, Y and Z. Sheets 2, 4 and 6, usually along with several other similar parallel corrugated sheets, are brought together in contact, along line A-A', with every other sheet having its ridges running at right-angles to the adjacent sheet, thereby forming a corrugated sheet sandwich. To fit a cylindrical reactor, as shown in cross-section in FIGS. 3a and 3b, the corrugated sheets are trimmed in area to provide, when stacked together, an over-all cylindrical shape to fit or pack the internal space formed by the reactor wall. Thus, the preferred stationary mixing elements comprise multi-layered, corrugated sheets wherein the ridges of adjacent sheets run at about right-angles to each other to form open, intersecting channels to direct fluids radially and generally upward while causing the fluid streams of each channel to partially split and mix with the stream with which it intersects. It is also preferred that individual stationary mixing elements are positioned concentrically at 90° rotation relative to each other, as depicted in cross-section in FIGS. 3a and 3b. This 90° relationship of the elements permits two dimensional mixing as the reaction mass proceeds beyond the first element.

The stationary mixing elements broadly include from at least 2 up to 40 units, preferably from 4 to about 20 units and will be within the active reaction zone such that reactant streams are directed in plug-flow or in radially intersecting paths in the generally axial flow of the gas-liquid, gas-gas reactants. The mixing elements are fabricated of suitable corrosion-resistant material, e.g. fluoropolymer resins, glass, or noble metals such as tantalum or niobium.

A specific description of the apparatus used in the experiments described in the following examples is now set forth. The apparatus comprised a vertical tubular 4 inch internal diameter reactor constructed of sections of glass, glass-lined steel, and fluoropolymer-lined steel, flanged pipe fittings (spools, tees, and crosses), with an overall length of 14 feet. The reactor was connected to a vertical ("side-arm") heat exchanger by an overflow conduit about 12 feet from the bottom of the reactor, and by a recycle conduit about 2 feet from the bottom of the reactor. The reactor was configured for continuous operation.

The system was charged with a mixture containing about 70 vol. % methane sulfonic acid (MSA), 26% water, and 4% hydrogen chloride (HCl). The reactor was filled to about 1 foot below the overflow conduit. Chlorine gas (99.5% pure) was sparged into the reactor on automatic flow control via a feed port about 3½ feet from the bottom of the reactor (a drilled fluoropolymer feed tube extending across the cross-section of the reactor served as the sparger). Vaporized methyl mercaptan (99% pure RSX) was sparged into the reactor on automatic flow control via a feed port about 5 feet from the bottom of the reactor (a drilled fluoropolymer feed tube extending across the cross-section of the reactor served as the sparger).

The reaction of chlorine with the mercaptan was very vigorous, evolving gaseous HCl, which was vented (along with unreacted chlorine and mercaptan) from the top of the reactor to a condenser, with the condensate being returned to the reactor, and the non-condensibles sent to a caustic scrubber via a pressure-control valve. An automatic pressure controller maintained the top of the reactor at the target pressure.

The gas evolution created bubbles which expanded the reaction liquid above the level of the overflow conduit, inducing a circulation through the side-arm exchanger, which was used to remove the exothermic heat of reaction. Coolant flow to the side-arm exchanger was adjusted by means of an automatic temperature control to maintain the temperature of the (cooled) liquid recirculating to the reactor at the target temperature. [The reactor was operated above 80° C., so that the primary reaction product was the sulfonic acid (MSA), with a minor percentage of unhydrolyzed methane sulfonyl chloride (MSC)]. A portion of the recirculating reaction liquid was taken-off on automatic flow control via the bottom of the reactor as crude MSA product. The take-off rate was adjusted to maintain the target specific gravity. The liquid level in the reactor was maintained at about 2 inches above the overflow conduit by feeding make-up water to the reactor on automatic level control. The makeup water was combined with the recycle condensate and introduced to the reactor via a liquid feed port about 2 ½ feet above the bottom of the reactor. The "active" zone of the reactor was the 7 foot long section of the reactor between the mercaptan feed port and the overflow conduit to the heat exchanger. The bottom 5 feet of the "active" zone was constructed of glass piping, to allow visual observation of the bubble dynamics in the active zone.

Example 1a (Comparative)

In this example, the "active" zone of the reactor contained no internal mixing devices. The reaction temperature was 98° C. and the reactor top pressure was 1.5 psig. The mercaptan feedrate was 7.3 lb/hr, and the chlorine feedrate was 33.2 lb/hr., corresponding to 3.15% excess chlorine. The crude take-off rate was adjusted to maintain the specific gravity of the reaction liquid at 1.33, corresponding to about 63 wt. % MSA in the crude product.

The crude MSA of this example contained 103 ppm of "oxidizable" impurities, primarily methane methyl thiosulfonate (MMTS), and dimethyl disulfide (DMDS).

Example 1b

In this example, the operating conditions were identical to Example 1a, except that the lower 52 inches of the "active zone" of the reactor was packed with 13 intersecting, corrugated-plate style, stationary mixing elements (manufactured by Koch Engineering, Type "SMV-AY"), made from Teflon PFA fluoropolymer, and as generally shown in FIGS. 2, 3a and 3b of the drawing. Each element was 4 inches in diameter by 4 inches long with ½ inch pitch from horizontal between corrugations. Adjacent mixing elements were positioned concentrically and at a 90° rotation relative to each other.

The crude MSA of this example contained 9 ppm of "oxidizable" impurities.

The emplacement of the stationary mixing elements resulted in an 11-fold reduction in oxidizable impurities (compared to Example 1a). It is expected that other types and models of stationary mixing elements will provide comparable results since the various types of static mixer units are designed to induce a similar flow pattern (plug-flow) and intimate contacting of the fluids.

Example 2a (Comparative)

In this example, the "active" zone of the reactor contained no internal mixing devices. The reaction temperature was 98° C. and the reactor top pressure was 10.5 psig. The mercaptan feedrate was 5.6 lb/hr, and the chlorine feedrate was 24.9 lb/hr, corresponding to 0.85% excess chlorine. The crude take-off rate was adjusted to maintain the specific gravity of the reaction liquid at 1.38, corresponding to about 76 wt. % MSA in the crude product. The crude MSA contained 51 ppm of "oxidizable" impurities. 4.6% of the sulfur value in the mercaptan feed was lost to the reactor vent gas.

Example 2b

In this example, the operating conditions were identical to example 2a, except that the lower 52 inches of the "active" zone" of the reactor was packed with stationary mixing elements, as described in Example 1b.

The crude MSA contained no detectable "oxidizable" impurities (the analytical detection limit was 5 ppm). 2.8% of the sulfur value in the mercaptan feed was lost to the reactor vent gas.

The emplacement of the stationery mixing elements resulted in at least a 10-fold reduction in oxidizable impurities, as well as a 40% reduction in mercaptan yield losses (compared to Example 2a), and possibly completely eliminated the oxidizable impurities.

Example 3a (Comparative)

In this example, the "active" zone of the reactor contained no mixing internal devices. The reaction temperature was 113° C. The reactor top pressure was 1.5 psig. The mercaptan feedrate was 5.6 lb/hr, and the chlorine feedrate was 24.8 lb/hr, corresponding to 0.44% excess chlorine. The crude take-off rate was adjusted to maintain the specific gravity of the reaction liquid at 1.38, corresponding to about 76 wt. % MSA in the crude product.

The crude MSA contained 149 ppm of "oxidizable" impurities. 3.0% of the sulfur value in the mercaptan feed was lost to the reactor vent gas.

Example 3b

In this example, the operating conditions were identical to Example 3a, except that the lower 52 inches of the "active" zone of the reactor was packed with stationary mixing elements, as described in Example 1b.

The crude MSA contained 66 ppm "oxidizable" impurities. 2.4% of the sulfur value in the mercaptan feed was lost to the reactor vent gas.

The emplacement of the stationary mixing elements resulted in a 90 ppm reduction in oxidizable impurities, as well as a 20% reduction in mercaptan yield losses (compared to Example 3a).

Observations of the Foregoing Examples

At start-up of the foregoing experiments, the initial charge of liquid to the reactor was not fully saturated with HCl. Under this condition, the HCl generated by reaction was absorbed into the liquid, rather than evolving as a vapor, until the liquid was saturated with HCl.

During the start-up of the runs described in Examples 1b, 2b, and 3b (active zone packed with stationary mixing elements), it was observed that only the 6–12 inches above the bottom of the active zone showed significant bubbling; this was the region where the chlorine and mercaptan were being solubilized and reacted; the HCl produced by reaction was absorbed in the unsaturated liquid, leaving the remainder of the "active" zone quiescent until the entire inventory of recirculating liquid was saturated with HCl. Thereafter, the entire "active" zone was bubbling vigorously due to the rise of the evolved HCl which could no longer be absorbed by the saturated liquid.

In contrast, during start-up of the runs described in Examples 1a, 2a, and 3a (no internal mixing devices in the "active" zone), bubbles were observed to rise throughout the length of the active zone, even though the liquid was not yet saturated with HCl. These bubbles originated below the active zone, and were unreacted bubbles of chlorine and/or mercaptan, which did not contact each other, emerging from the reaction liquid as unconverted feed materials.

These results demonstrate that the emplacement of stationary mixers in the reactor improves the volumetric efficiency of the reactor.

Example 4

The observations presented above also demonstrate that the emplacement of stationary mixing elements in the reactor converts the practical throughput limitation from a volumetric basis (mole/hr-ft$^3$), as described in claims 1 and 3 of the U.S. Pat. No. 3,626,004, to a cross-sectional area basis (mole/hr-ft$^2$), since above the first 6–12 inches, the "active" zone of the reactor may be of arbitrary length, consistent with other considerations such as equipment spacing, residence time requirements for ASC hydrolysis, and the like.

In this example, the lower part of the active "zone" of the reactor was packed with stationary mixing elements as described in Example 1b. The reaction temperature was 102° C. and the reactor top pressure was 0.8 psig. The mercaptan feedrate was 12 lb/hr, and the chlorine feedrate was 55 lb/hr, corresponding to 3.95% excess chlorine. Further, the mercaptan throughput was 2.86 lbmole/hr-ft$^2$. No hydraulic limitations (e.g., slugging flow or excessive back-pressure) were evident; indeed, the throughput was limited by the ability of the feed system to sustain higher feedrates. Since the reaction effectively took place in the first 6–12 inches of the "active" zone (as discussed in the above Observations), and the stationary mixing elements displace about 14% of the volume that they occupy, the "local" volumetric throughput in this example was between 3.3 and 6.6 lbmole/hr-ft$^3$.

The emplacement of the stationary mixer elements allows the reactor to be operated well above the upper limit (1 lbmole/hr-ft$^3$) of volumetric throughputs taught in claim 1 of the U.S. Pat. No. 3,626,004, and two-to-three order of magnitude greater than the preferred range (0.005–0.03 lbmole/hr-ft$^3$) taught in claim 3 of that patent.

What is claimed is:

1. A process for the preparation of a product consisting essentially of alkane sulfonic acid, comprising continuously reacting a compound of the formula RSX, where X is hydrogen or a radical of the formula —SR$^1$ and R and R$^1$ are alkyl groups having one to 20 carbon atoms, with at least a stoichiometric amount of chlorine, in a reaction zone free of moving, mechanical agitating means and containing aqueous hydrochloric acid at a reactant feedrate at least sufficient to achieve a vigorous evolution of hydrochloride gas, passing the contents of said reaction zone through, and in contact with stationary mixing elements to promote plug-flow, withdrawing hydrochloride gas, and separately withdrawing said product from the reactor, wherein the temperature of the reaction ranges from about 85° to about 115° C.

2. A process for the preparation of a product consisting essentially of alkane sulfonic acid, comprising continuously reacting a compound of the formula RSX, where X is hydrogen or a radical of the formula —SR$^1$ and R and R$^1$ are alkyl groups having one to 20 carbon atoms, with at least a stoichiometric amount of chlorine in a reaction zone free of moving, mechanical agitating means and containing aqueous hydrochloric acid at a reactant feedrate at least sufficient to achieve a vigorous evolution of hydroxychloride gas, passing the contents of said reaction zone through, and in contact with stationary mixing elements to promote plug-flow, withdrawing hydrochloride gas, and separately withdrawing said product from the reactor, wherein said stationary means comprises multi-layered, intersecting corrugated sheets forming open fluid channels to direct fluids radially toward and away from the walls of said reaction zone in a generally upward path, said stationary means substantially filling said reaction zone and wherein the temperature of the reaction ranges from about 85° to about 115° C.

3. The process of claim 2 wherein said stationary means comprises at least two units of said multi-layered, intersecting corrugated sheets positioned concentrically with each other and each unit being at a 90° rotation with respect to its adjacent units.

4. The method of claim 2 wherein R has from one to six carbon atoms and X is hydrogen.

5. The process of claim 4 wherein the feedrate of the RSX reactant to the reaction zone ranges from about 0.5 to about 8.0 lbmole/hr.-ft$^2$ based on the cross-sectional area of said reaction zone.

6. The process of claim 5 wherein R is methyl.

* * * * *